US011090107B2

(12) United States Patent
Mathur et al.

(10) Patent No.: US 11,090,107 B2
(45) Date of Patent: Aug. 17, 2021

(54) ABLATION MEDICAL DEVICES

(71) Applicant: BOSTON SCIENTIFIC SCIMED, INC., Maple Grove, MN (US)

(72) Inventors: Prabodh Mathur, Laguna Niguel, CA (US); Henry H. Lee, Mission Viejo, CA (US); Andres Dandler, Newport Coast, CA (US); Flavio K. Ono, Laguna Niguel, CA (US); Joseph A. Levendusky, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 731 days.

(21) Appl. No.: 14/796,711

(22) Filed: Jul. 10, 2015

(65) Prior Publication Data
US 2016/0008053 A1    Jan. 14, 2016

Related U.S. Application Data

(60) Provisional application No. 62/023,621, filed on Jul. 11, 2014.

(51) Int. Cl.
*A61B 18/14* (2006.01)
*A61B 18/00* (2006.01)
*A61B 17/00* (2006.01)

(52) U.S. Cl.
CPC .......... *A61B 18/14* (2013.01); *A61B 18/1492* (2013.01); *A61B 2017/00526* (2013.01);
(Continued)

(58) Field of Classification Search
CPC ................ A61B 18/14; A61B 18/1492; A61B 2017/00526; A61B 2018/00053;
(Continued)

(56) References Cited

U.S. PATENT DOCUMENTS 5,156,151 A * 10/1992 Imran .................... A61N 1/056
                                                              600/375
5,228,442 A *  7/1993 Imran .................. A61B 5/0422
                                                              600/374
(Continued)

FOREIGN PATENT DOCUMENTS

EP           0644738 B1     3/2000
WO   WO2014/070999    *  5/2014  ............... A61N 1/05

OTHER PUBLICATIONS

"Examination Report," for Australian Patent Application No. 2015287652 dated Jan. 24, 2017 (3 pages).
(Continued)

*Primary Examiner* — Jaymi E Della
(74) *Attorney, Agent, or Firm* — Pauly, DeVries Smith & Deffner LLC

(57) ABSTRACT

Medical devices and methods for making and using medical devices are disclosed. An example medical device includes an ablation system. The ablation system may include an elongate shaft having a distal region. A plurality of ablation tines may be disposed at the distal region. Each of the ablation tines may include a tubular member having a flexible circuit disposed therein. The flexible circuit may include a substrate, one or more electrodes coupled to the substrate, and a temperature sensor coupled to the substrate and positioned adjacent to the one or more electrodes. The plurality of ablation tines may include a first ablation tine and a second ablation tine. A pair of bipolar electrodes may defined by a first electrode disposed at the first ablation tine and a second electrode disposed at the second ablation tine.

19 Claims, 20 Drawing Sheets

(52) U.S. Cl.
CPC ............... *A61B 2018/0016* (2013.01); *A61B 2018/00053* (2013.01); *A61B 2018/00577* (2013.01); *A61B 2018/00642* (2013.01); *A61B 2018/00702* (2013.01); *A61B 2018/00791* (2013.01); *A61B 2018/00797* (2013.01); *A61B 2018/143* (2013.01); *A61B 2018/1425* (2013.01); *A61B 2018/1475* (2013.01)

(58) Field of Classification Search
CPC .. A61B 2018/0016; A61B 2018/00577; A61B 2018/00642; A61B 2018/00702; A61B 2018/00791; A61B 2018/00797; A61B 2018/1425; A61B 2018/143; A61B 2018/1475
See application file for complete search history.

(56) References Cited

U.S. PATENT DOCUMENTS

| | | | |
|---|---|---|---|
| 5,238,004 | A | 8/1993 | Sahatjian et al. |
| 5,415,166 | A | 5/1995 | Imran |
| 5,456,254 | A * | 10/1995 | Pietroski ............... A61B 5/0422 600/372 |
| 5,465,717 | A * | 11/1995 | Imran ................... A61B 5/0422 600/374 |
| 5,499,981 | A * | 3/1996 | Kordis ................. A61B 5/0422 606/41 |
| 5,772,609 | A | 6/1998 | Nguyen et al. |
| 6,139,510 | A | 10/2000 | Palermo |
| 6,508,803 | B1 | 1/2003 | Horikawa et al. |
| 2004/0158239 | A1* | 8/2004 | Behl ................... A61B 18/1477 606/41 |
| 2005/0054905 | A1* | 3/2005 | Corl ................... A61B 5/14539 600/309 |
| 2006/0058676 | A1* | 3/2006 | Yagi ........................ A61B 8/12 600/459 |
| 2006/0244177 | A1* | 11/2006 | Kaneto ................... A61B 5/03 264/248 |
| 2007/0219551 | A1* | 9/2007 | Honour ................ A61B 5/0422 606/41 |
| 2008/0255553 | A1 | 10/2008 | Young et al. |
| 2009/0143651 | A1* | 6/2009 | Kallback ............ A61B 5/02007 600/301 |
| 2009/0240249 | A1 | 9/2009 | Chan et al. |
| 2010/0094279 | A1* | 4/2010 | Kauphusman ....... A61B 5/0422 606/41 |
| 2011/0024186 | A1* | 2/2011 | Receveur ............... A61N 1/056 174/70 R |
| 2012/0150009 | A1* | 6/2012 | Ollivier ................ A61B 5/0215 600/374 |
| 2012/0172696 | A1* | 7/2012 | Kallback .............. A61B 5/0215 600/373 |
| 2012/0271138 | A1* | 10/2012 | Kordis ................. A61B 5/0422 600/375 |
| 2013/0282084 | A1* | 10/2013 | Mathur .................... A61N 5/00 607/101 |
| 2014/0018788 | A1* | 1/2014 | Engelman .............. A61B 18/18 606/33 |
| 2015/0105645 | A1* | 4/2015 | Subramaniam ...... A61B 5/6859 600/374 |

OTHER PUBLICATIONS

"International Preliminary Report on Patentability," for PCT Application No. PCT/US2015/040017 dated Jan. 26, 2017 (9 pages).
"International Search Report and Written Opinion," for PCT Application No. PCT/US2015/040017 dated Oct. 14, 2015 (12 pages).
"Second Office Action," for Chinese Patent Application No. 201580032698.8 dated Apr. 28, 2019 (9 pages) with English Summary.
"Communication Pursuant to Article 94(3) EPC," for European Patent Application No. 15742461.5 dated May 7, 2020 (5 pages).
"Response to Communication Pursuant to Article 94(3) EPC," for European Patent Application No. 15742461.5 filed Sep. 16, 2020 (14 pages).

* cited by examiner

ABLATION MEDICAL DEVICES

CROSS-REFERENCE TO RELATED APPLICATIONS

This application claims priority under 35 U.S.C. § 119 to U.S. Provisional Application Ser. No. 62/023,621, filed Jul. 11, 2014, the entirety of which is incorporated herein by reference.

TECHNICAL FIELD

The present disclosure pertains to medical devices, and methods for manufacturing medical devices. More particularly, the present disclosure pertains to medical devices for ablating tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An embodiment medical device may include an ablation system. The ablation system includes an elongate shaft having a distal region. A plurality of ablation tines is disposed at the distal region. Each of the ablation tines includes a tubular member having a flexible circuit disposed therein. The flexible circuit includes a substrate, one or more electrodes coupled to the substrate, and a temperature sensor coupled to the substrate and positioned adjacent to the one or more electrodes. The plurality of ablation tines includes a first ablation tine and a second ablation tine. A pair of bipolar electrodes is defined by a first electrode disposed at the first ablation tine and a second electrode disposed at the second ablation tine.

Alternatively or additionally to the embodiment above, the plurality of ablation tines includes a distal array of ablation tines and a proximal array of ablation tines.

Alternatively or additionally to any of the embodiments above, the distal array of ablation tines is circumferentially offset from the proximal array of ablation tines.

Alternatively or additionally to any of the embodiments above, the flexible circuit includes a first trace disposed along a first side of the substrate, the first trace being coupled to the temperature sensor.

Particularly, the flexible circuit may include a second trace disposed along a second side of the substrate, the second trace being coupled to the first trace by a via. Alternatively or additionally to any of the embodiments above, the flexible circuit includes a second trace disposed along a second side of the substrate, the second trace being coupled to the first trace by a via.

Furthermore, the one or more electrodes may be disposed along the second side of the substrate. Alternatively or additionally to any of the embodiments above, the one or more electrodes are disposed along the second side of the substrate.

Alternatively or additionally to any of the embodiments above, the flexible circuit includes an active trace disposed along a first side of the substrate, wherein the temperature sensor is coupled to the active trace, and wherein a return trace coupled to the active trace is disposed along the first side of the substrate.

Alternatively or additionally to any of the embodiments above, the flexible circuit includes one or more additional temperature sensors.

Alternatively or additionally to any of the embodiments above, the flexible circuit is folded within the tubular member.

Alternatively or additionally to any of the embodiments above, further comprising a processor coupled to the ablation tines.

Particularly, the processor may be capable of modulating power delivered to the pair of bipolar electrodes based on feedback from the temperature sensor. Alternatively or additionally to any of the embodiments above, the processor is capable of modulating power delivered to the pair of bipolar electrodes based on feedback from the temperature sensor.

In another embodiment, a medical device for ablating tissue is disclosed. The medical device includes an elongate shaft having a distal region. A distal array of ablation tines is disposed along the distal region. A proximal array of ablation tines is disposed adjacent to the distal array of ablation tines. The distal array of ablation tines, the proximal array of ablation tines, or both are capable of shifting between a first configuration and an expanded configuration. The distal array of ablation tines and the proximal array of ablation tines include a plurality of tubular members. Each tubular member has a flexible circuit disposed therein. The flexible circuit includes a substrate, one or more electrodes disposed along the substrate and electrical coupled to the tubular member, and a temperature sensor coupled to the substrate and positioned adjacent to the one or more electrodes. The plurality of tubular members define one or more pairs of bipolar electrodes. A processor is coupled to the distal array of ablation tines and the proximal array of ablation tines. The processor is capable of modulating power delivered to the one or more electrodes based on feedback from the temperature sensor.

Alternatively or additionally to any of the embodiments above, the distal array of ablation tines is circumferentially offset from the proximal array of ablation tines.

Alternatively or additionally to any of the embodiments above, the flexible circuit includes one or more additional temperature sensors.

Alternatively or additionally to any of the embodiments above, the flexible circuit is folded within the tubular member.

Alternatively or additionally to any of the embodiments above, the flexible circuit includes a first trace disposed along a first side of the substrate, the first trace being coupled to the temperature sensor.

Alternatively or additionally to any of the embodiments above, the flexible circuit includes a second trace disposed along a second side of the substrate, the second trace being coupled to the first trace by a via.

Alternatively or additionally to any of the embodiments above, the one or more electrodes are disposed along the second side of the substrate.

Alternatively or additionally to any of the embodiments above, the flexible circuit includes an active trace disposed along a first side of the substrate, wherein the temperature sensor is coupled to the active trace, and wherein a return trace coupled to the active trace is disposed along the first side of the substrate.

In another embodiments, a method for ablating tissue is disclosed. The method includes positioning a medical device adjacent to a target tissue. The medical device includes an elongate shaft having a distal region. A distal array of ablation tines is disposed along the distal region. A proximal array of ablation tines is disposed adjacent to the distal array of ablation tines. The distal array of ablation tines, the proximal array of ablation tines, or both are capable of shifting between a first configuration and an expanded configuration. The distal array of ablation tines and the proximal array of ablation tines include a plurality of tubular members. Each tubular member has a flexible circuit disposed therein. The flexible circuit includes a substrate, one or more electrodes disposed along the substrate and electrical coupled to the tubular member, and a temperature sensor coupled to the substrate and positioned adjacent to the one or more electrodes. The plurality of tubular members define one or more pairs of bipolar electrodes. A processor is coupled to the distal array of ablation tines and the proximal array of ablation tines. The processor is capable of modulating power delivered to the one or more electrodes based on feedback from the temperature sensor. The method also includes activating the one or more electrodes. Activating the one or more electrodes includes modulating power delivered to the one or more electrodes over a time period with the processor based on feedback from the temperature sensor.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
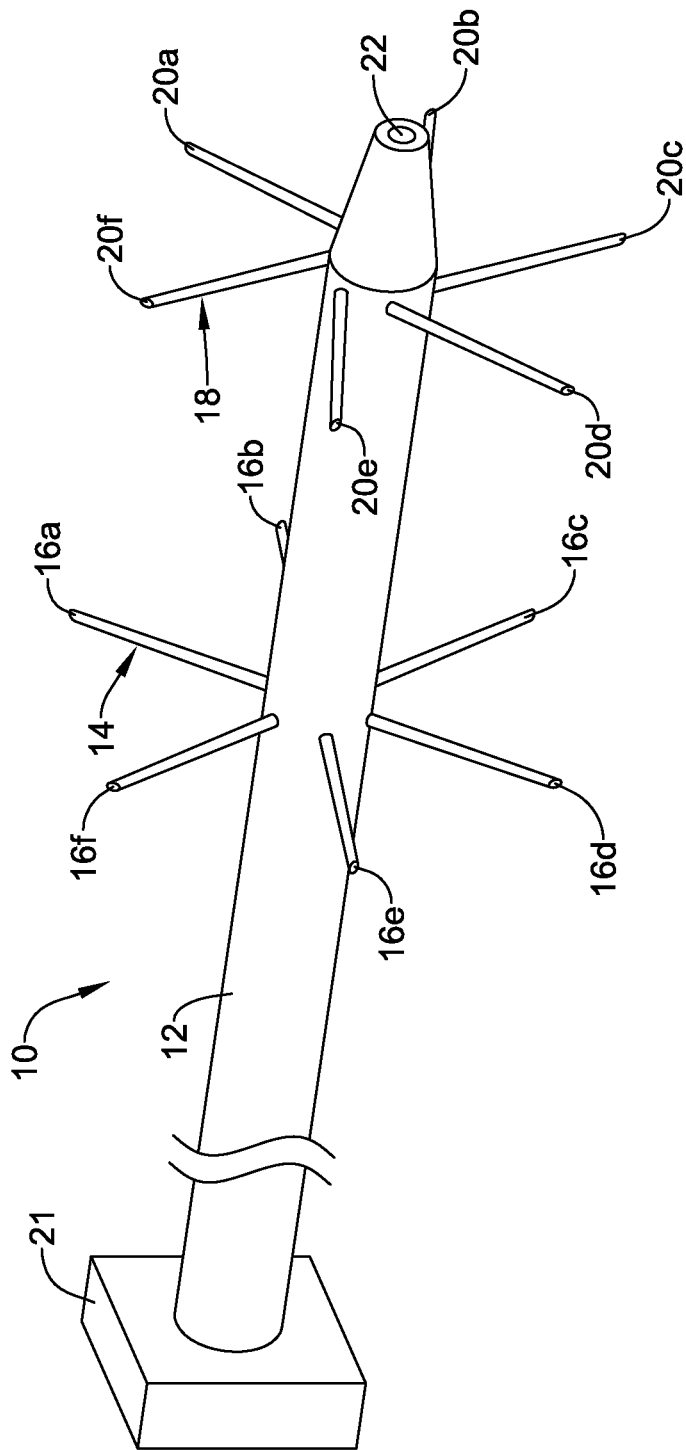
FIG. 1 is a perspective side view of an embodiment of a medical device according to the invention.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Radiofrequency ablation systems may be utilized to create lesions within a target tissue such as a tumor. An example radiofrequency ablation system may include a single tine monopolar system that includes a needle electrode. The needle electrode may be activated to create relatively discrete lesions. In order to create larger lesions, the needle electrode may be repositioned, for example repeatedly repositioned, and activated at different locations. While effective, the lesions may be inconsistent and/or non-homogenous. Other example radiofrequency ablation systems may include a plurality of monopolar tines. Such systems may overcome some of the limitations of the single tine systems. However, these systems could overheat, which could also result in non-homogenous lesions.

At least some of the medical devices, ablation devices, and/or ablation device systems disclosed herein are designed to overcome at least some of the limitations of single and/or multiple tine monopolar ablation systems. For example, the ablation devices disclosed herein may utilize arrays of ablation tines that may be capable of bipolar energization. The devices disclosed herein may be capable of creating relatively homogenous lesions of a variety of different sizes (e.g., up to about 10-250 $cm^3$ or more). Furthermore, the devices disclosed herein may be designed to improve the quality of the ablation and/or reduce the ablation procedure time. Some additional details regarding the devices/systems are disclosed herein.

FIG. 1 illustrates an embodiment of a medical device 10 according to the invention. Medical device 10 may include a shaft 12. A proximal array of tines 14 may be coupled to shaft 12, for example along a distal region of shaft 12. Proximal array 14 may include a plurality of individual tines such as tines 16a/16b/16c/16d/16e/16f. A distal array of tines 18 may be coupled to shaft 12, for example along a distal region of shaft 12. Distal array 18 may include a plurality of individual tines such as tines 20a/20b/20c/20d/20e/20f. In this example, proximal array 14 includes six tines 16a/16b/16c/16d/16e/16f and distal array 18 also includes six tines 20a/20b/20c/20d/20e/20f. This is not intended to be limiting. Proximal array 14 and distal array 18 may include a suitable number of tines such as two, three, four, five, six, seven, eight, or more tines. Furthermore, the number of tines in arrays 14/18 may or may not be the same. The tines in arrays 14/18 may have a diameter in the range of about 0.001-0.01 inches (e.g., about 0.00254-0.0254 cm) and may have lengths on the order of 0.1 cm to several centimeters.

Proximal array 14 and/or distal array 18 may project radially outward from shaft 12. In doing so, tines 16a/16b/16c/16d/16e/16f may be generally planar. Likewise, tines 20a/20b/20c/20d/20e/20f may also be generally planar. In at least some instances, tines 16a/16b/16c/16d/16e/16f and tines 20a/20b/20c/20d/20e/20f may lie within generally parallel planes. In other embodiments, the planes may not be parallel with one another. These are just examples. Other arrangements are contemplated.

Any one or all of tines 16a/16b/16c/16d/16e/16f/20a/20b/20c/20d/20e/20f (for simplicity the following discussion will refer to tine 16a but the discussion may be applicable to any or all of tines 16a/16b/16c/16d/16e/16f/20a/20b/20c/20d/20e/20f) may take the form of solid wire or tubular member. For example, tine 16a may include an inert, electrically conductive member taking the form of a tube. Tine 16a may include an electrode assembly or flexible circuit disposed therein. The structure of the flexible circuit may be the same or similar to the flexible circuits disclosed herein. For example, the flexible circuits may include a substrate, one or more electrodes, and one or more temperature sensors. In some of these and in other embodiments, one or more electrodes may be coupled to tine 16a (e.g., along an outer surface of tine 16a).

The one or more electrodes disposed within tine 16a may be in electrical contact with tine 16a such that tine 16a may be considered as an electrode or ablation member. Accordingly, energy supplied to the one or more electrodes of the flexible circuit may be conducted to tine 16a and, ultimately, to a target tissue. The tines 16a/16b/16c/16d/16e/16f/20a/20b/20c/20d/20e/20f may be electrically insulated from one another. In addition, because device 10 may include arrays 14/18 of tines 16a/16b/16c/16d/16e/16f/20a/20b/20c/20d/20e/20f, tines 16a/16b/16c/16d/16e/16f/20a/20b/20c/20d/20e/20f may define one or more pairs of bipolar electrodes. The pairs of bipolar electrodes may be defined with a given array (e.g., tine 16a and tine 16b may define a pair of bipolar electrodes) or across arrays (e.g., tine 16a and tine 20a may define a pair of bipolar electrodes).

As shown schematically in FIG. 1, a controller or processor 21 may be coupled to device 10. Processor 21 may be electrically coupled to (e.g., via wires or other suitable structures) the electrodes and temperature sensors disposed along/within the various tines 16a/16b/16c/16d/16e/16f/20a/20b/20c/20d/20e/20f. In at least some embodiments, processor 21 may include one or more RF generators. Other processors and/or power sources are contemplated.

Processor 21 may be capable of modulating the amount of power supplied to each of the electrodes based on temperature feedback provided by the temperature sensors. For example, processor 21 may be capable of reducing (or stopping) power supplied to a particular electrode or set of electrodes when temperature feedback from temperature sensors positioned adjacent to the electrodes indicates a greater extent of heating than desired (e.g., the temperature adjacent to a subset of electrodes is approaching, has reached, or has exceeded a pre-determined temperature threshold). Analogously, processor 21 may also be capable of throttling up the power to a subset of electrodes where the temperature adjacent to these electrodes is lower than desired. Processor 21 may also be capable of modulating the amount of power supplied to each of the electrodes based on impedance sensing in addition to or alternatively to temperature sensing. Modulation of power may allow for more even heating and/or lesion creation as well as more homogenous lesions. In addition, the phase angle between the voltage and the current may also be measured, which may allow for more accurate calculation of impedance and/or power.

In addition, processor 21 may also be capable of determining and/or choosing the particular tines 16a/16b/16c/16d/16e/16f/20a/20b/20c/20d/20e/20f that may be utilized to form a pair of bipolar electrodes that would best fulfill the needs of a given intervention. For example, if addition heat energy is needed adjacent to or between a particular pair of tines (e.g., between tine 16a and tine 20a), processor 21 may be capable of activating the one or more electrodes within tines 16a/20a in the appropriate manner so as to define the suitable pair of bipolar electrodes. To this end, processor 21 may be capable of switching the electrodes within tines 16a/20a (and/or any of tines 16a/16b/16c/16d/16e/16f/20a/20b/20c/20d/20e/20f) between a power/sourcing state, a ground/synching state, or an open/passing state. In other words, the electrodes within tines 16a/16b/16c/16d/16e/16f/20a/20b/20c/20d/20e/20f may be considered "tripolar". By doing so, processor 21 is capable of firing one pair of electrodes/tines or multiple pairs of electrodes/tines simultaneously. Fast switching relays may be used to change between these states. This may include the use of switching utilizing solid state circuitry.

In some instances, processor 21 may utilize an algorithm where temperature is used to determine where the greatest "need" (e.g., temperature is furthest below the target temperature). The electrode/tine where the greatest need is present may be defined as the "dominant" electrode. The dominant electrode may be set in the power/sourcing state. Electrodes that are above the target temperature threshold may be set to open/passing. In instances where only one electrode is below the target temperature, setting the electrodes above the temperature threshold to open/passing allows at least one pair of electrodes to fire (e.g., the dominant electrode below the temperature threshold paired with the electrode with the smallest temperature surplus). The remaining electrodes/tines may be set to ground/synching. After activating the dominant electrode (e.g., which may include utilizing a suitable PID calculation for the appropriate power levels), the process may be repeated. The time interval for each cycle of the algorithm may be on the order of about 1-30 ms, or about 1-25 ms, or about 1 ms, or about 10 ms, or about 25 ms. Other algorithms are contemplated. For example, algorithms are contemplated where instead of selecting only one dominant electrode, two (or more) electrodes with the highest temperature deficits could be selected as "co-dominant" electrodes.

Figure 2:
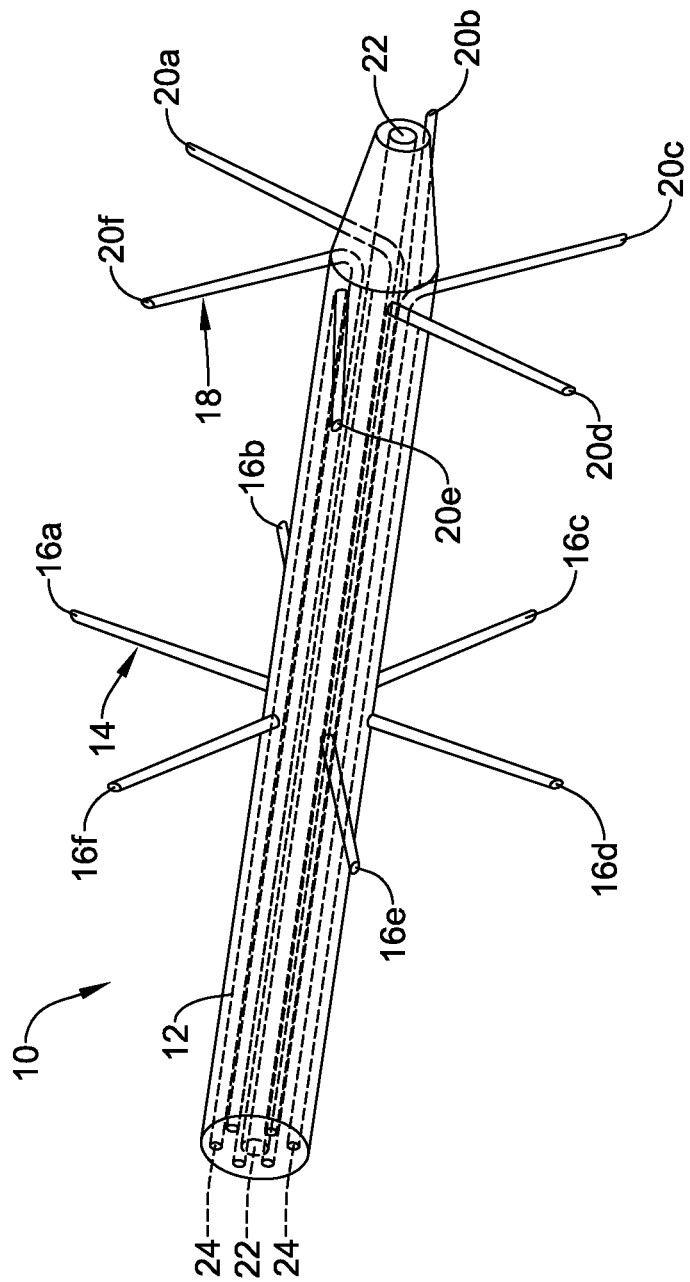
FIG. 2 is a perspective side view of the embodiment of the medical device according to FIG. 1.

Shaft 12 may define one or more lumens. For example, shaft 12 may define lumen 22, which may take the form of a guidewire lumen. As shown in FIG. 2, shaft 12 may also define a plurality of tine lumens 24. Tines 16a/16b/16c/16d/16e/16f and/or tines 20a/20b/20c/20d/20e/20f may be disposed within lumens 24. In some instances, each tine 16a/16b/16c/16d/16e/16f/20a/20b/20c/20d/20e/20f may lie within its own lumen 24. In other instances, one or more of tines 16a/16b/16c/16d/16e/16f/20a/20b/20c/20d/20e/20f may share one of lumens 24. Either way, tines 16a/16b/16c/16d/16e/16f/20a/20b/20c/20d/20e/20f may be movable within lumens 24. This may allow tines 16a/16b/16c/16d/16e/16f/20a/20b/20c/20d/20e/20f to shift between a first or "unexpanded" configuration where tines 16a/16b/16c/16d/16e/16f/20a/20b/20c/20d/20e/20f lie along shaft 12 and/or within lumens 24 and a second or "expanded" configuration where tines 16a/16b/16c/16d/16e/16f/20a/20b/20c/20d/20e/20f project radially from shaft 12.

Figure 3:
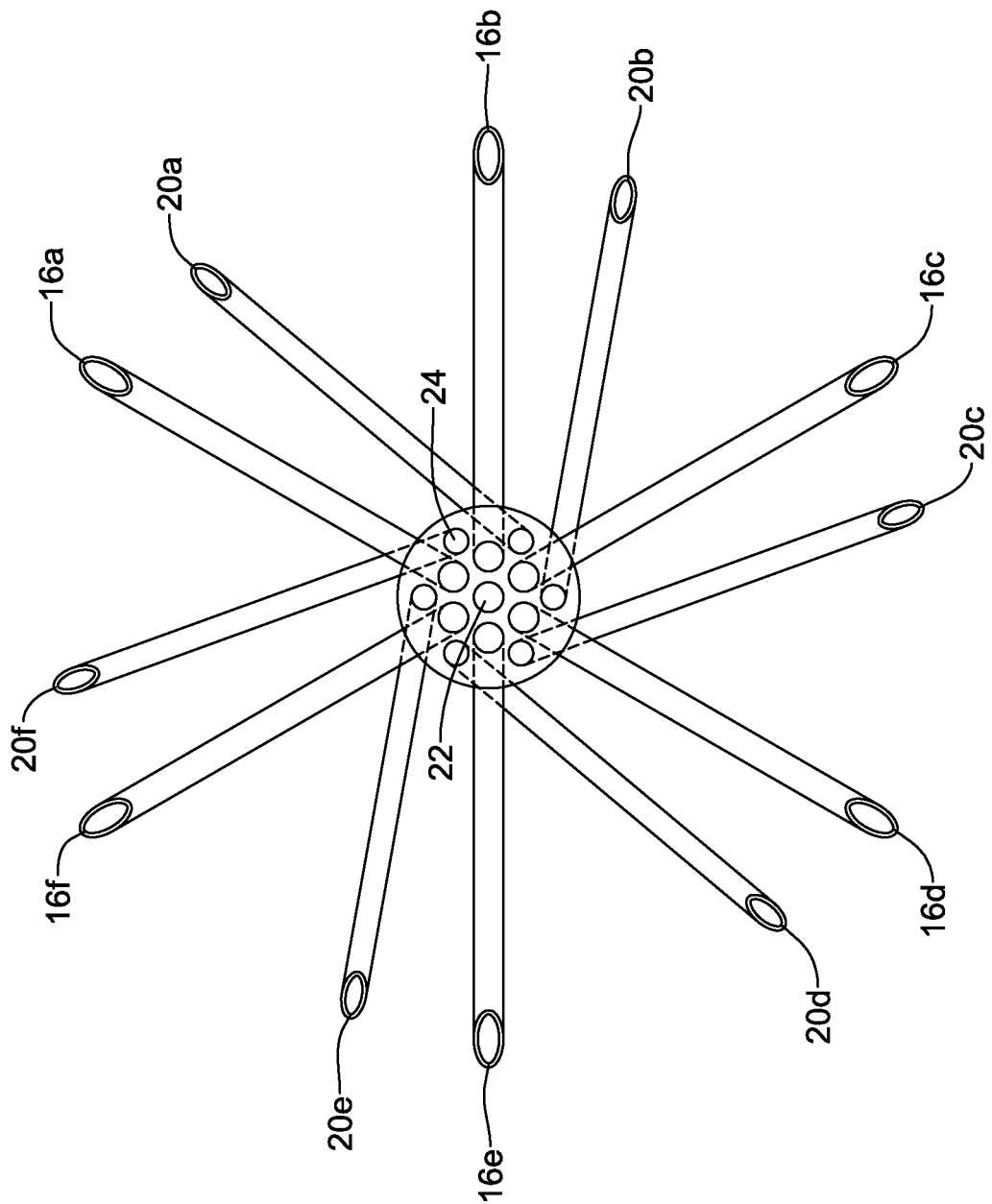
FIG. 3 is an end view of the embodiment of the medical device according to FIGS. 1 and 2.

In at least some embodiments, tines 16a/16b/16c/16d/16e/16f/20a/20b/20c/20d/20e/20f may be circumferentially aligned. For example, tine 16a may be circumferentially aligned with tine 20a. In other embodiments, tines 16a/16b/16c/16d/16e/16f and tines 20a/20b/20c/20d/20e/20f may be circumferentially offset from one another as shown in FIG. 3.

Figure 4:
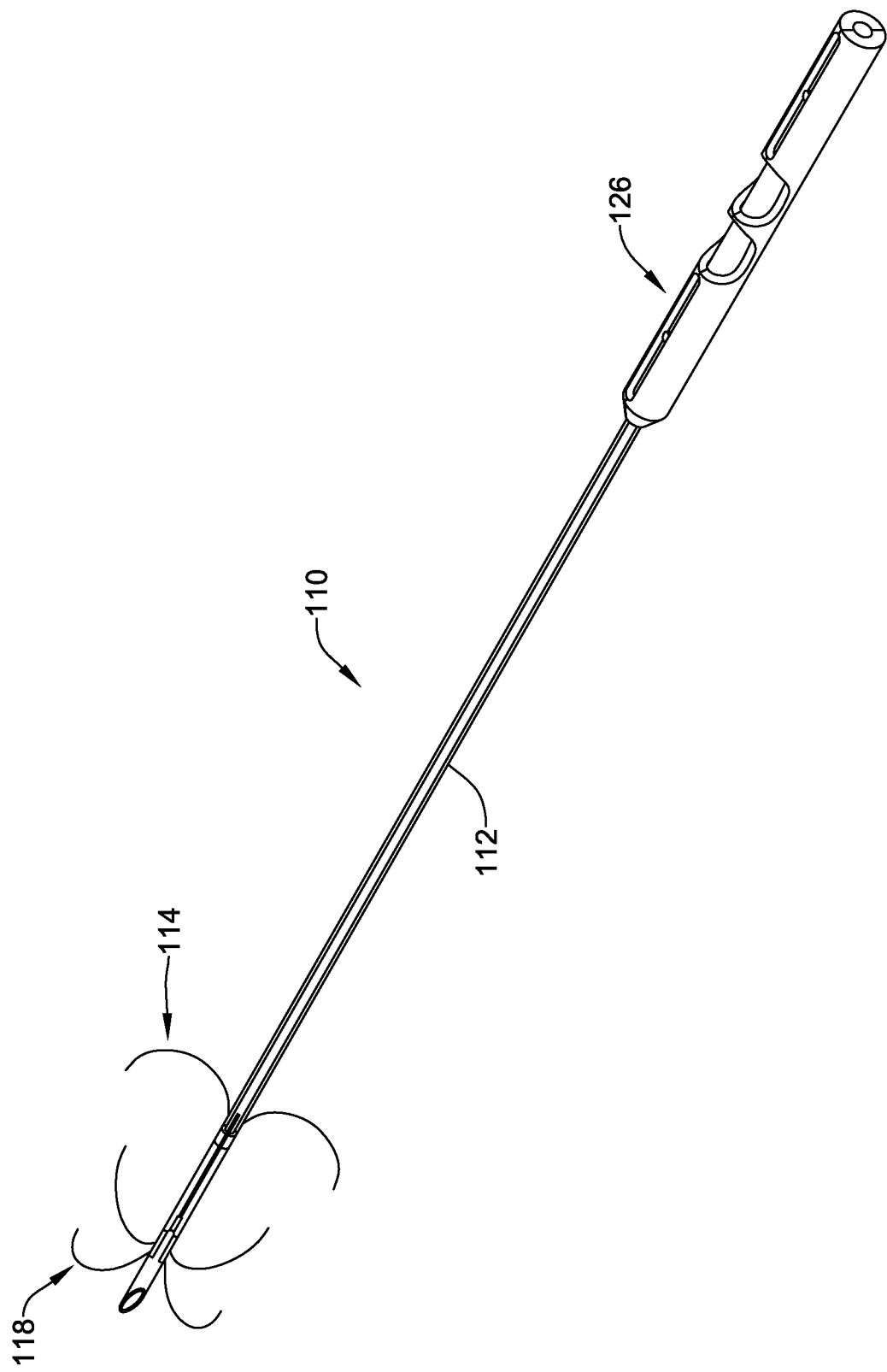
FIG. 4 is a perspective view of an example medical device.

FIG. 4 illustrates another example medical device 110 that may be similar in form and function to other medical devices disclosed herein. Device 110 may include shaft 112. A handle 126 may be coupled to the proximal end of shaft 112. Proximal and distal arrays of tines 114/118 may be disposed along shaft 112. In this embodiment, arrays 114/118 may include curved tines. The curved tines may allow arrays 114/118 to cover a greater amount of surface area.

Figure 5:
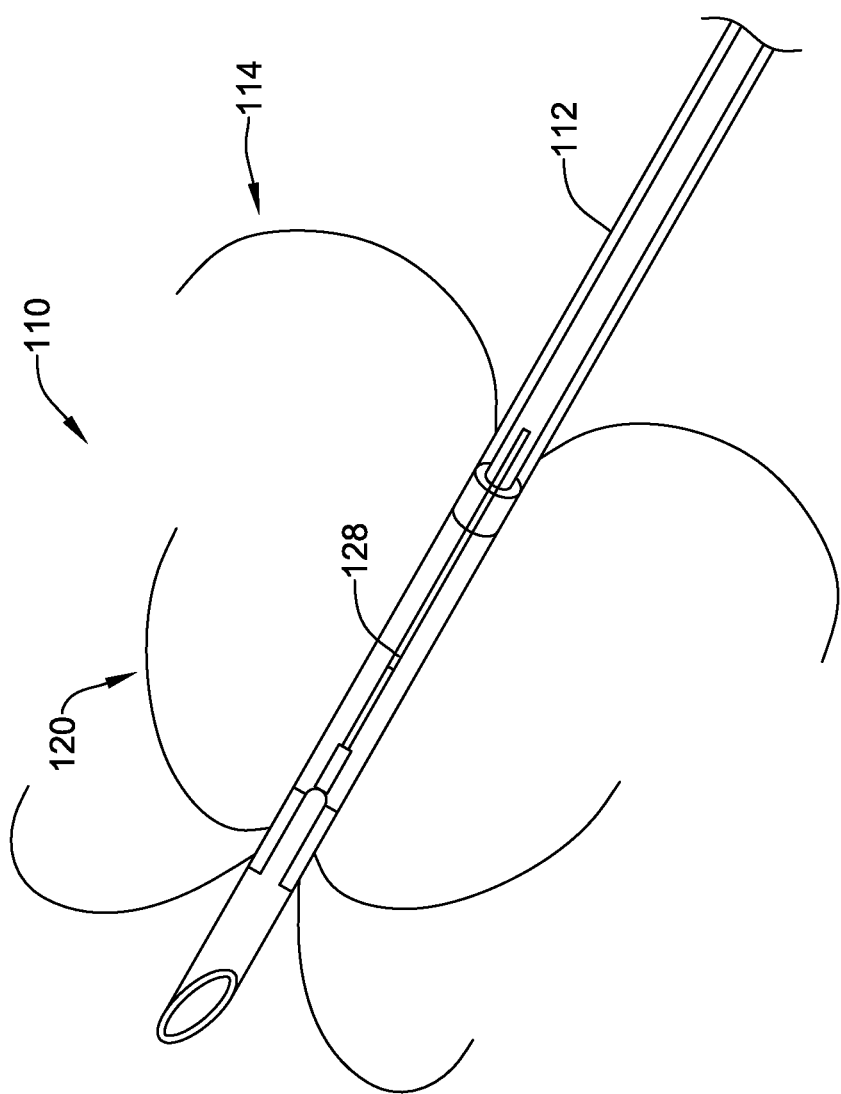
FIG. 5 is a perspective view of a portion of an example medical device.
Figure 6:
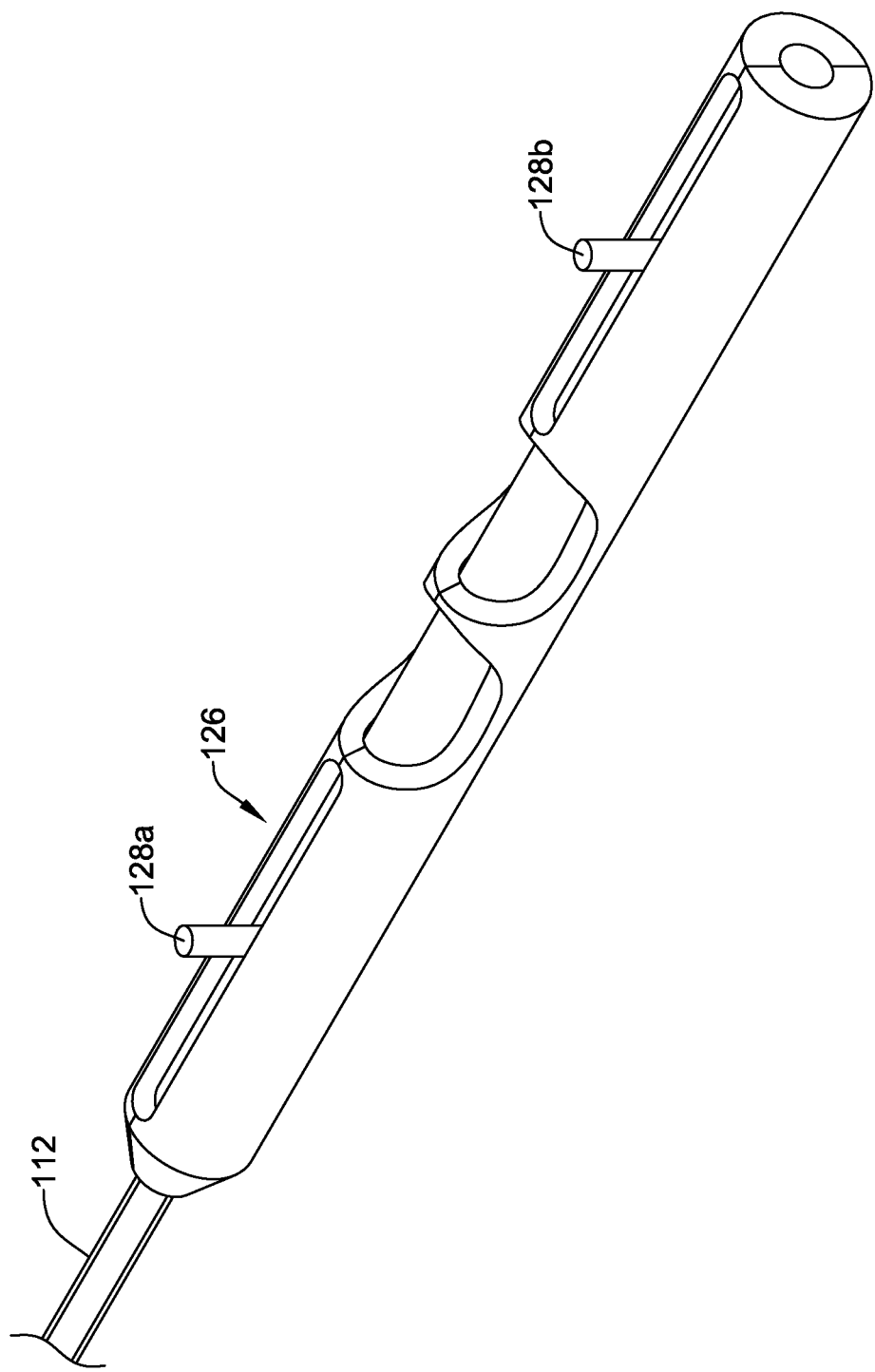
FIG. 6 is a perspective view of a portion of an example medical device.

A control wire 128 may be disposed within shaft 112 as shown in FIG. 5. Control wire 128 may be coupled to proximal and distal arrays of tines 114/118 so that proximal and distal arrays of tines 114/118 can be shifted between a first "non-expanded" configuration and an expanded configuration. In some instances, control wire 128 may provide power to flexible circuits disposed within proximal and distal arrays of tines 114/118. In other instances, separate power wires may be used. The separate power wires may be insulated from one another. In at least some embodiments, one or more control members 128a/128b may be disposed at handle 126 as shown in FIG. 6. Control members 128a/128b may be capable of shifting proximal and distal arrays of tines 114/118 between the non-expanded and expanded configurations.

Figure 7:
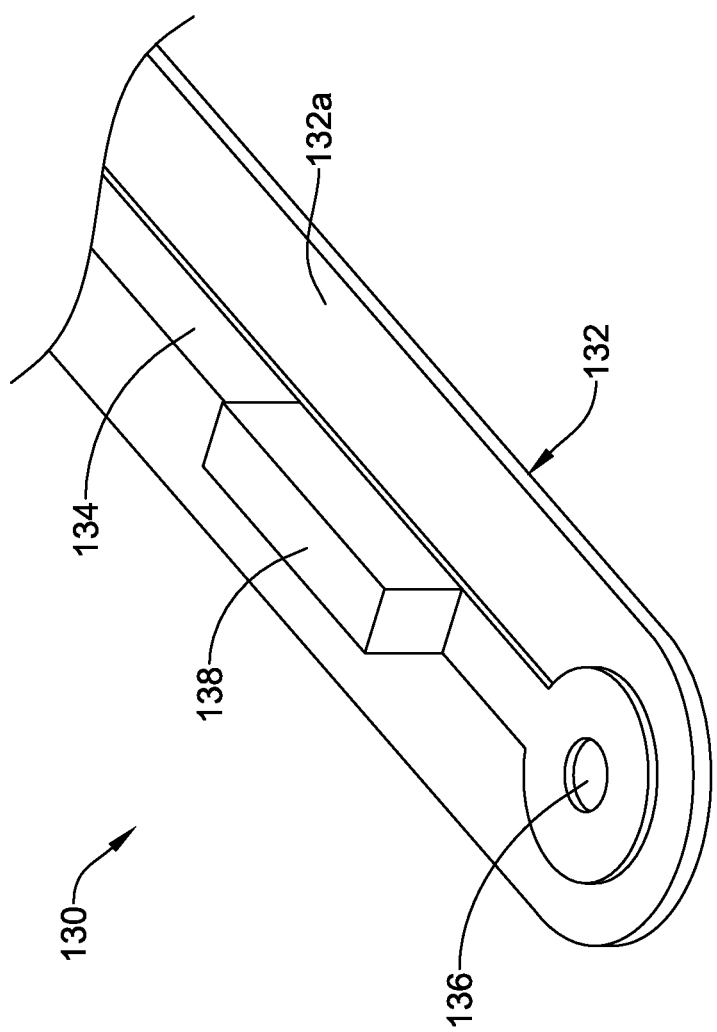
FIGS. 7-8 illustrate a portion of an example flexible circuit.
Figure 8:
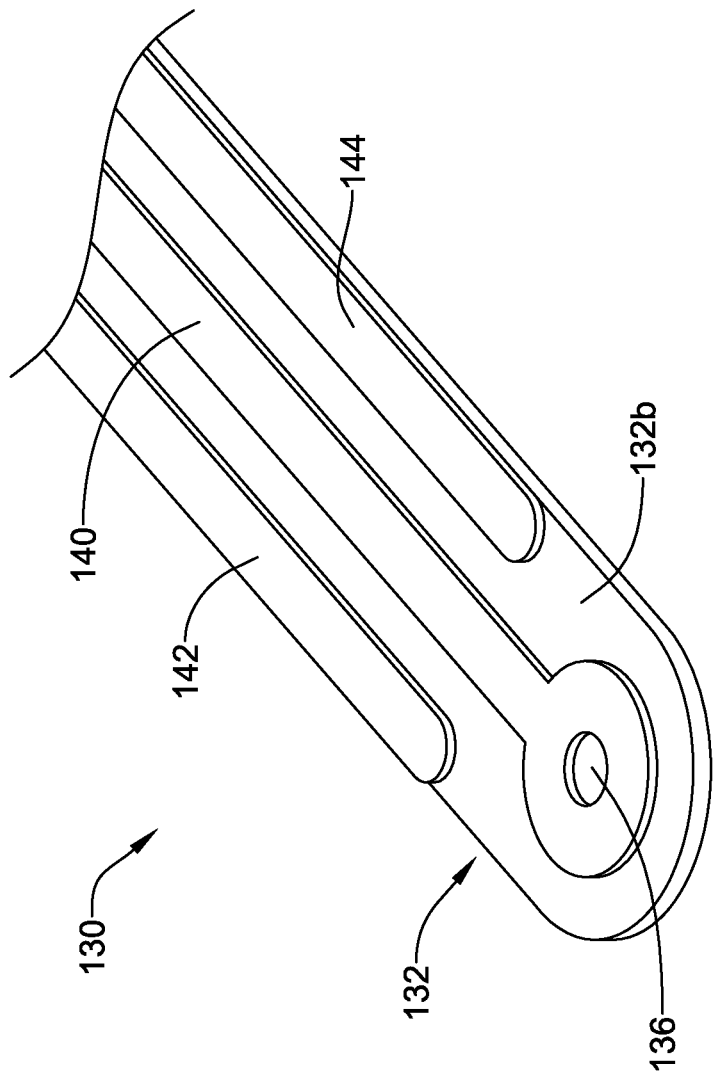

FIGS. 7-8 illustrate an example flexible circuit 130 that may be used with any of the devices disclosed herein. For example, flexible circuit 130 (and/or other flexible circuits disclosed herein) may be used by disposing flexible circuit 130 within the tines of the medical devices disclosed herein. Doing so may allow the tines to function as electrodes and/or an ablation surface. Flexible circuit 130 may include a substrate 132. Substrate 132 may include a suitable material such as one or more polymers. The polymer(s) may include a suitable material such as those disclosed herein. In at least some embodiments, substrate 132 may include a polyimide. A conductive member or trace 134 may extend along a first side 132a of substrate 132. Conductive trace 134 may be a printed, plated, deposited, or the like on substrate 132. In some embodiments, conductive trace 134 may include a conductive material such as copper, gold, gold-plated copper, conductive ink, or the like. A temperature sensor 138 may be coupled to conductive trace 134. Temperature sensor 138 may include a thermistor, a thermocouple, or another suitable temperature sensor. Conductive trace 134 may be electrically coupled to another conductive member or trace 140 on a second side 132b of substrate 132 by a via 136. One or more active traces, for example traces 142/144, may also be disposed along second side 132b. Traces 142/144 may define one or more electrodes. Manufacturing flexible circuit 130 may include suitably disposing trace 134 on substrate 132, coupling temperature sensor 138 to trace 134, forming via 136, and coupling traces 140/142/144 to substrate 132.

Figure 9:
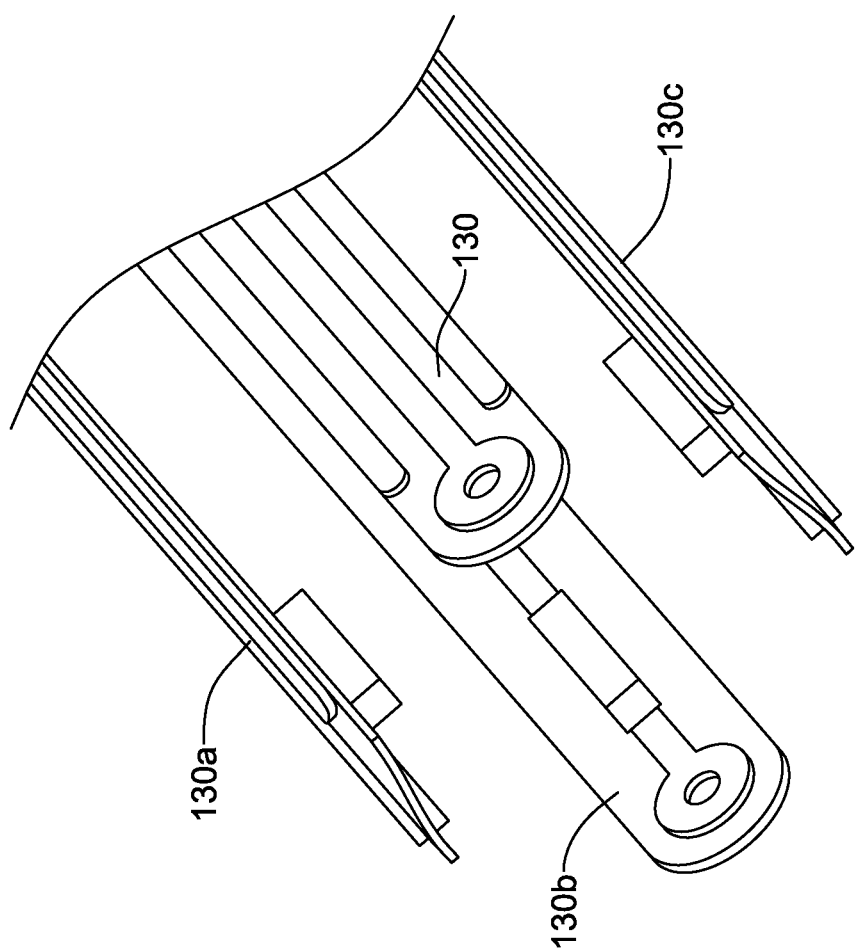
FIG. 9 illustrates a plurality of flexible circuits arranged in an array.
Figure 10:
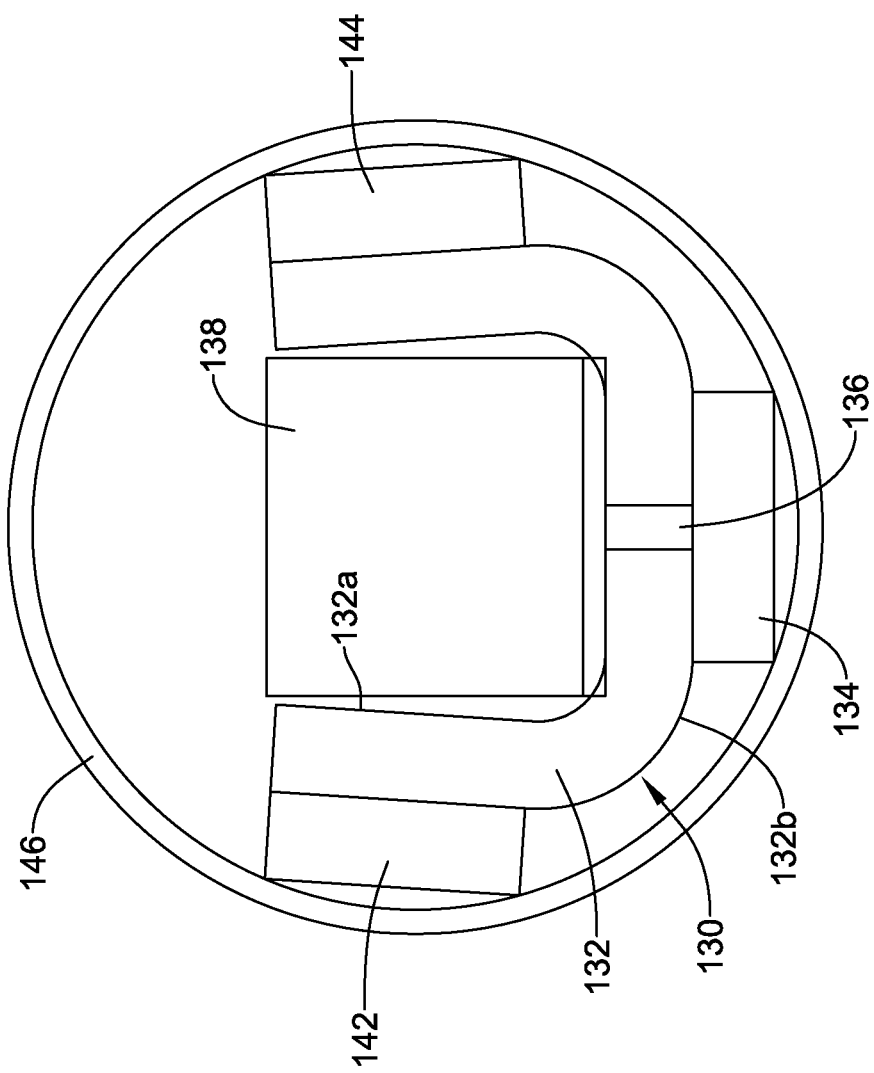
FIG. 10 illustrates an example flexible circuit disposed within a tubular tine.

A plurality of flexible circuits 130 may be arranged in an array as shown in FIG. 9. In this instance, four flexible circuits 130a/130b/130c/130d are arranged in an array. As such, flexible circuits 130a/130b/130c/130d may be disposed within a tine. For example, FIG. 10 illustrates flexible circuit 130 folded and disposed within a tine 146. In some instances, flexible circuit 130 may include one or more fold lines or scores to aid in folding flexible circuit 130 within tine 146. Thus, manufacturing medical device 110 may include folding flexible circuit 130 and disposing flexible circuit 130 within tine 146.

Figure 11:
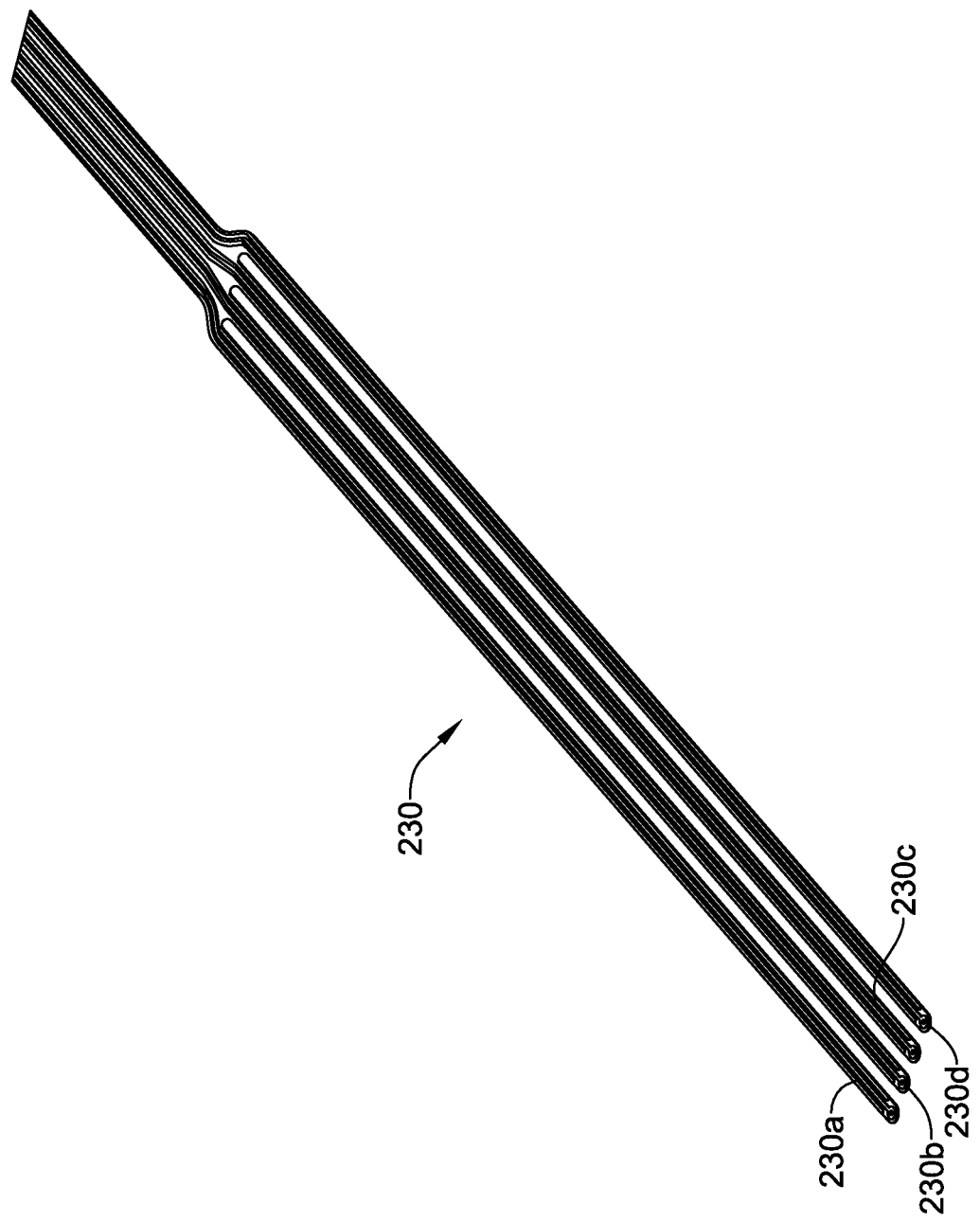
FIG. 11 illustrate an example flexible circuit assembly.
Figure 12:
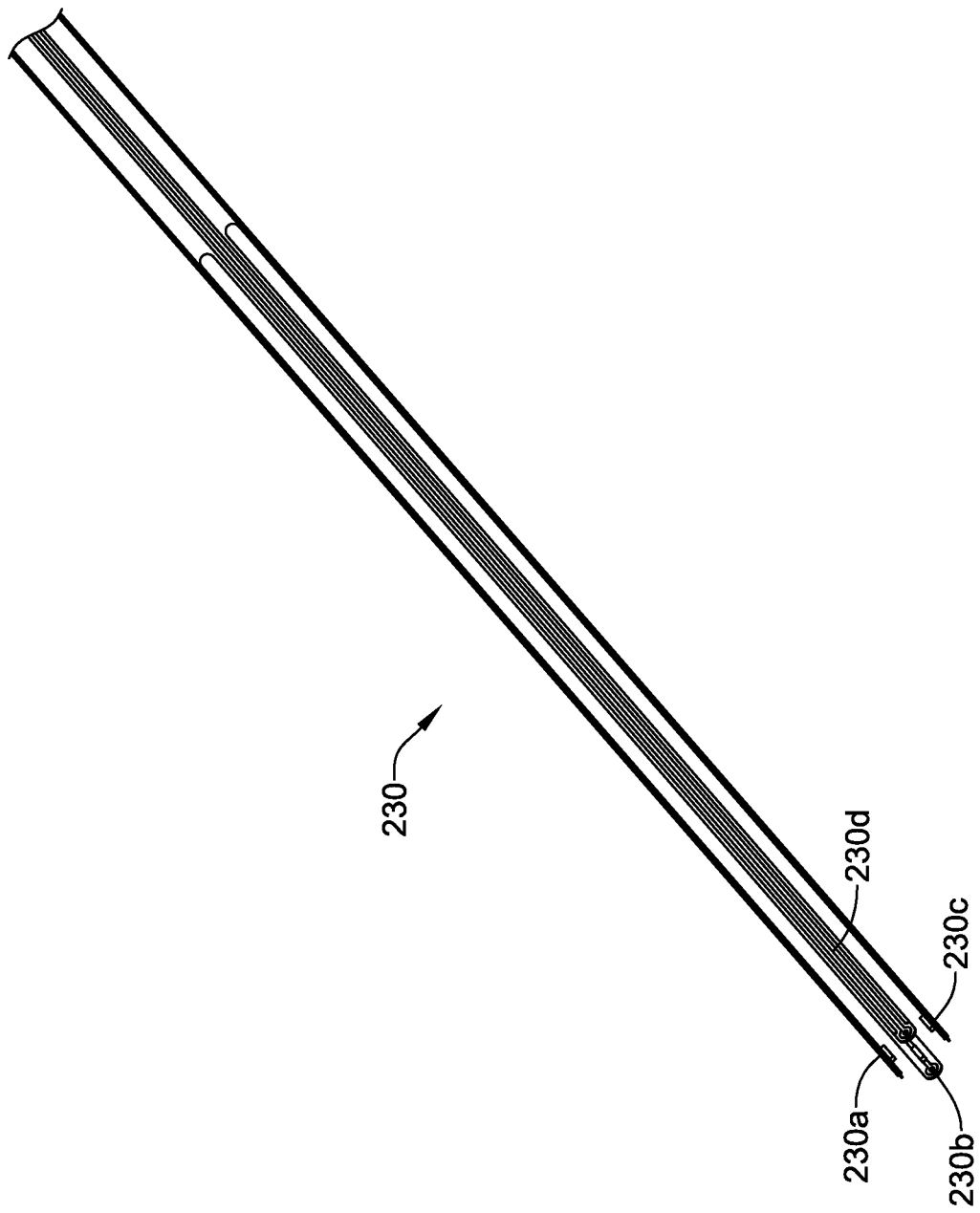
FIG. 12 illustrates an example flexible circuit assembly arranged in an array.

In some instances, flexible circuits 130 may be separate members that are disposed within individual tines (e.g., tine 146) of an array of tines. For example, an individual flexible circuit 130 is disposed in each of the individual tines 146. However, in other instances, a flexible circuit assembly 230 may be formed that includes a plurality of individual flexible circuit sections 230a/230b/230c/230d as shown in FIG. 11. Assembly 230 may be disposed in an array as shown in FIG. 12 and, ultimately, individual flexible circuit sections 230a/230b/230c/230d may be disposed within a tine.

Figure 13:
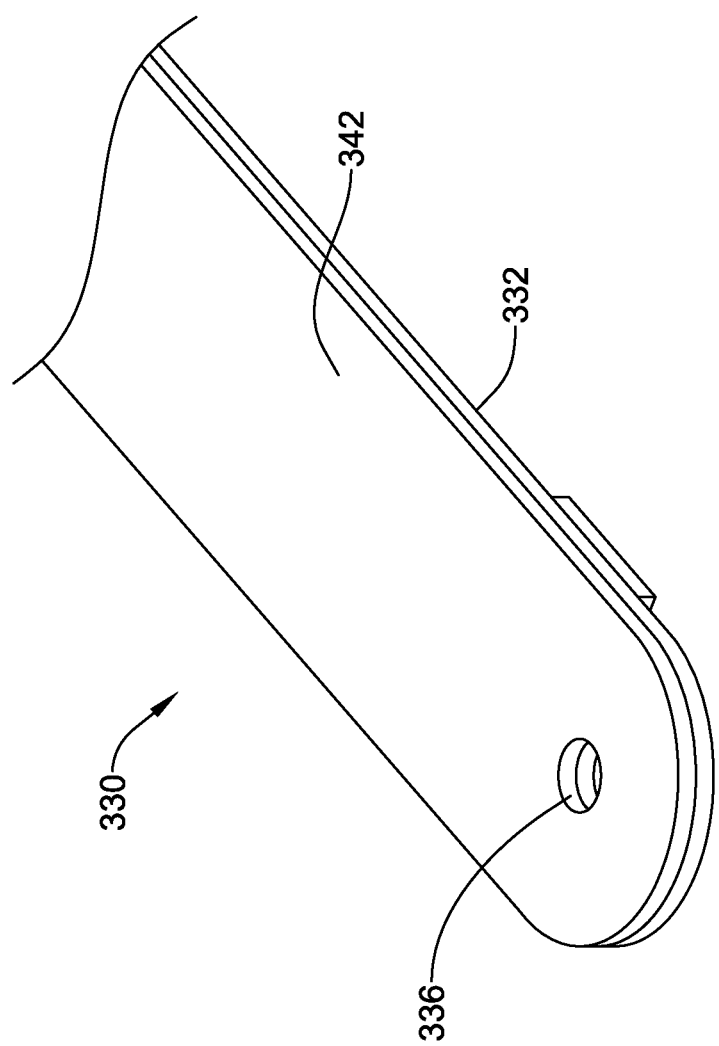
FIG. 13 illustrates a portion of an example flexible circuit.
Figure 14:
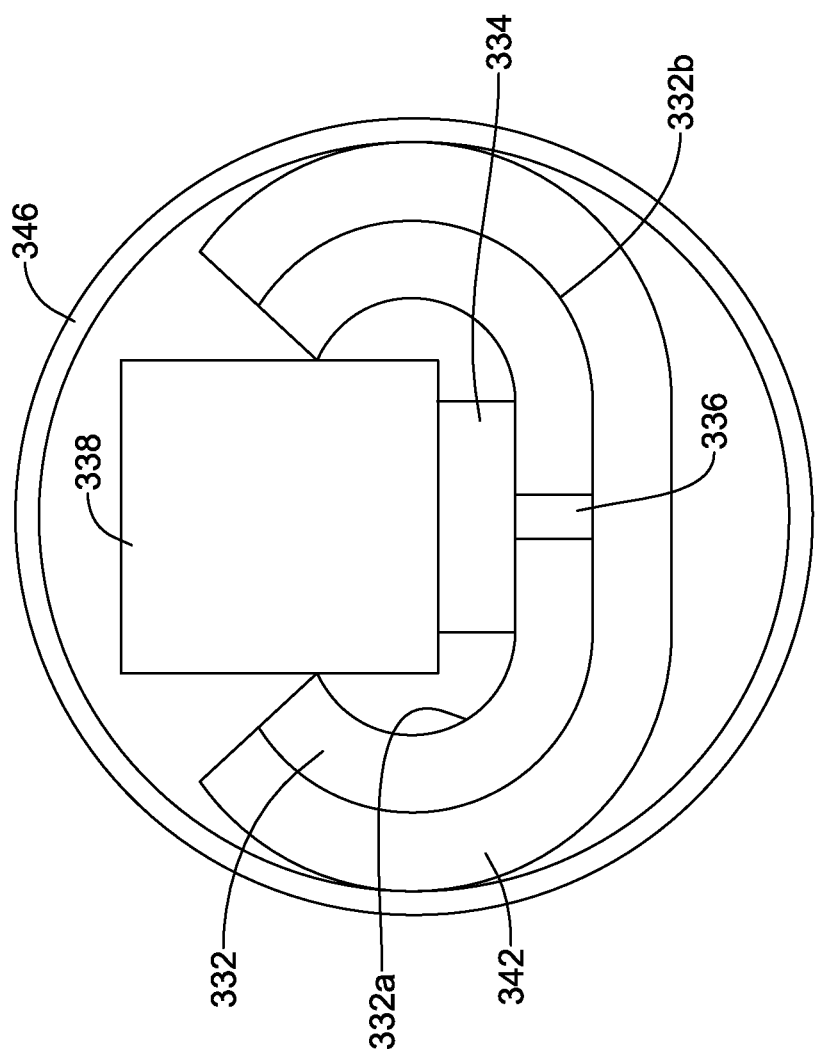
FIG. 14 illustrates an example flexible circuit disposed within a tubular tine.

FIGS. 13-14 illustrate another example flexible circuit 330 that may be similar to other flexible circuits disclosed herein. Flexible circuit 330 may include substrate 332. The first side 332a of substrate 332 may resemble first side 132a of flexible circuit 130 as shown in FIG. 7. For example first side 332a may include conductive trace 334 and temperature sensor 338. Rather than having a plurality of active traces, the second side 332b of substrate 332 may include a layer of conductive material 342. Layer 342 may be coupled to conductive trace 334 by via 336. Flexible circuit 330 may be folded and disposed within tine 346 (e.g., as shown in FIG. 14).

Figure 15:
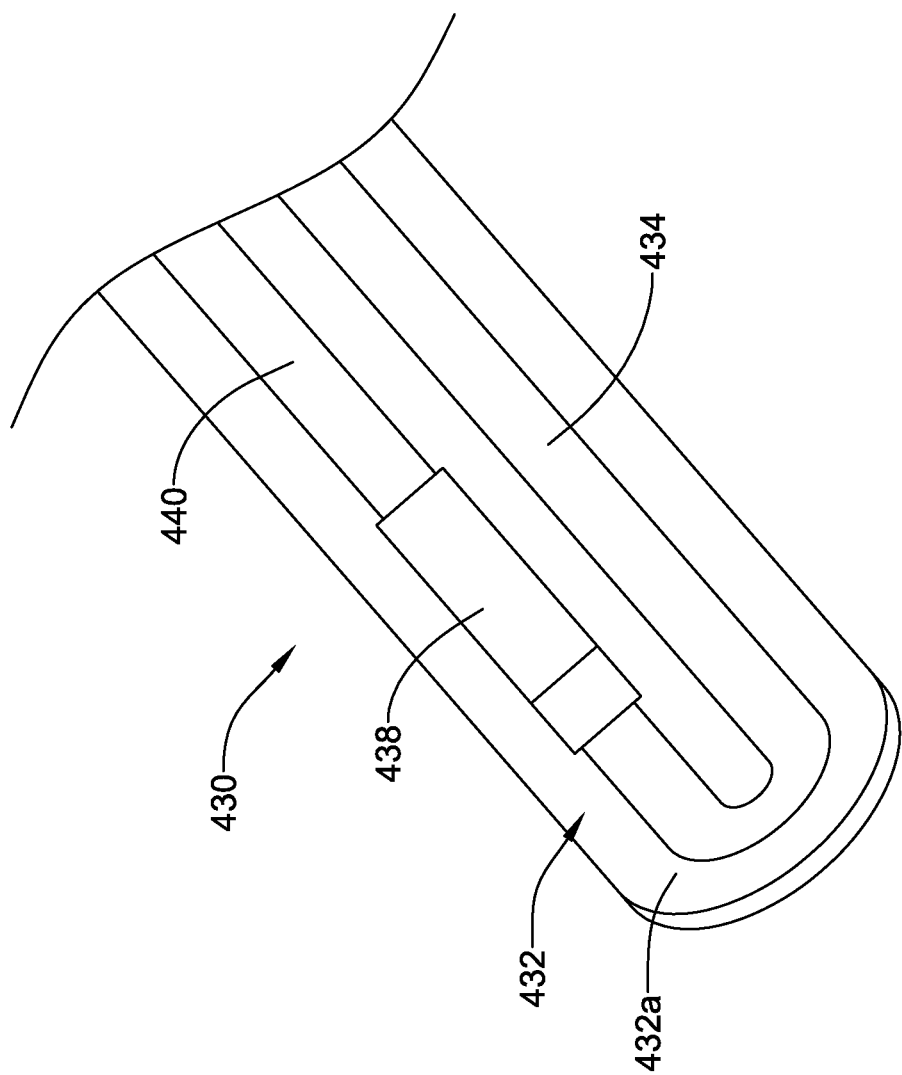
FIGS. 15-16 illustrate a portion of an example flexible circuit.
Figure 16:
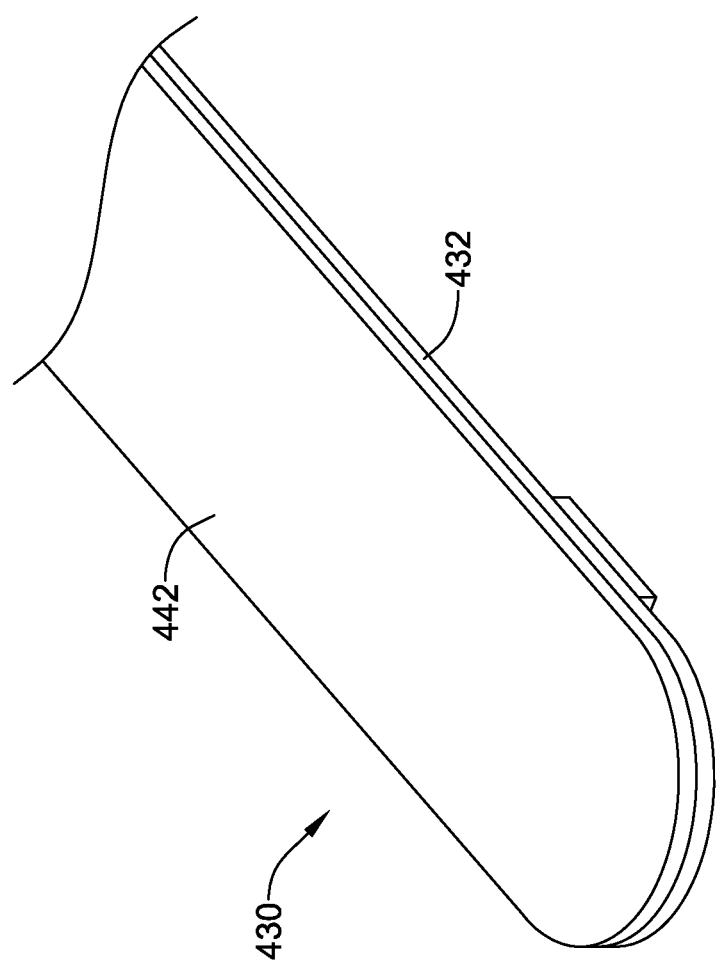

FIGS. 15-16 illustrate another example flexible circuit 430 that may be similar to other flexible circuits disclosed herein. Flexible circuit 430 may include substrate 432. Conductive trace 434 and return trace 440 may be disposed along first side 432a of substrate 432. Temperature sensor 438 may be coupled to traces 434/440. The second side of substrate 432 may include a layer of conductive material 442.

Figure 17:
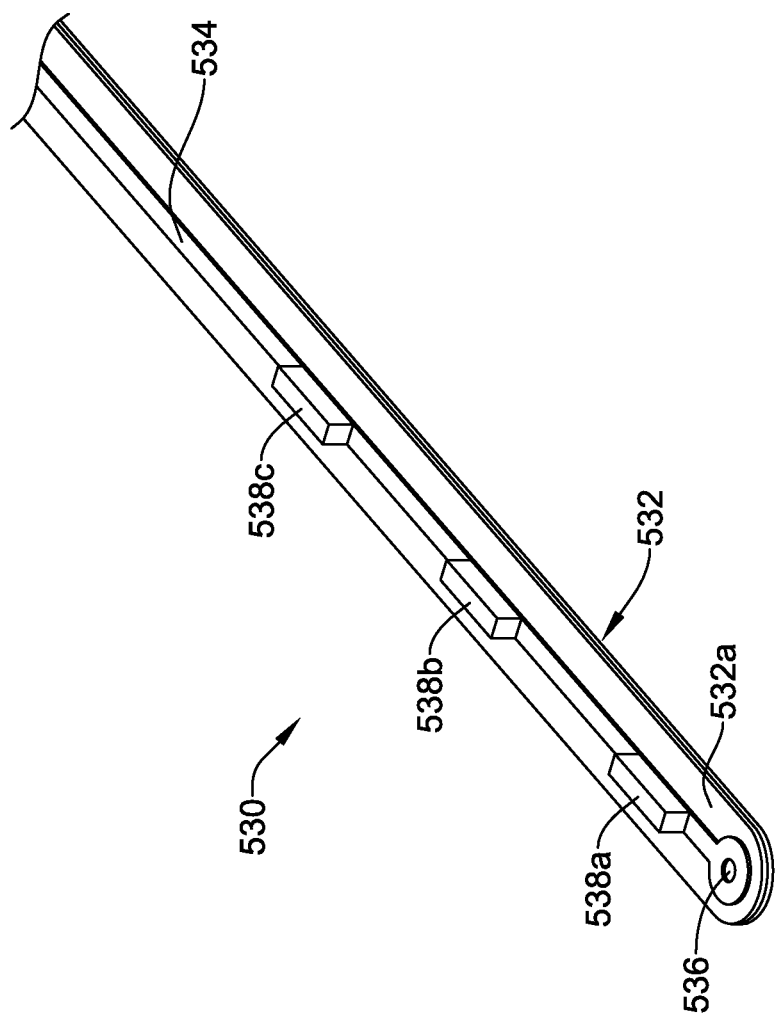
FIGS. 17-18 illustrate a portion of an example flexible circuit.
Figure 18:
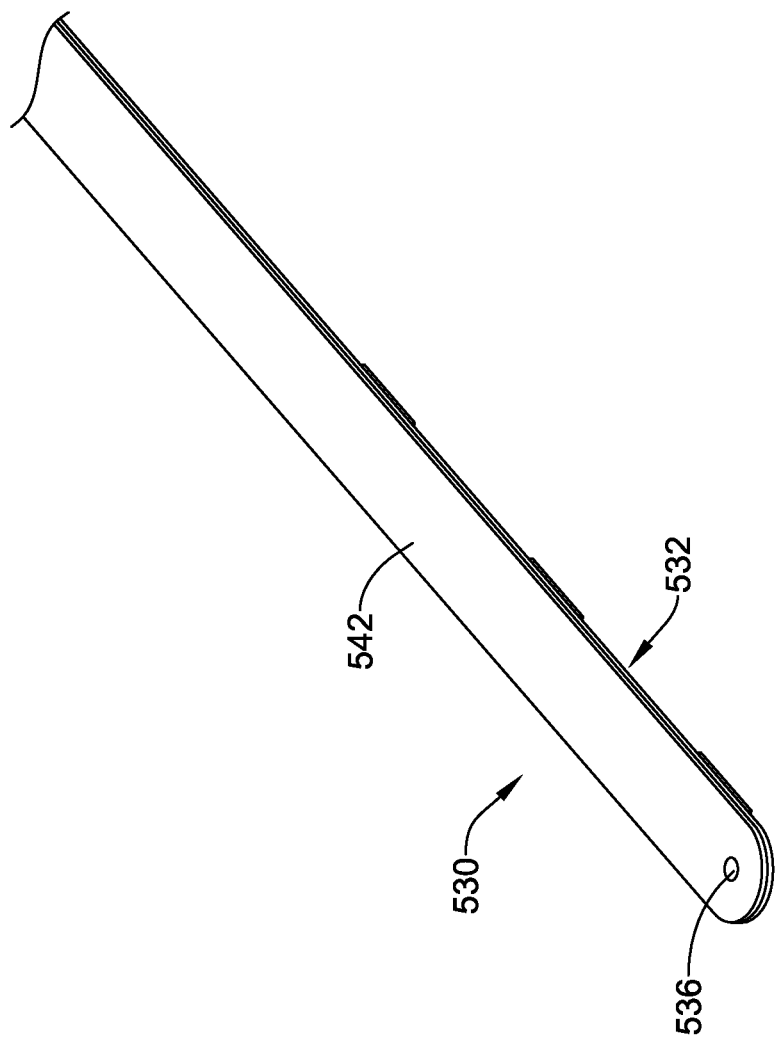

FIGS. 17-18 illustrate another example flexible circuit 530 that may be similar to other flexible circuits disclosed herein. Flexible circuit 530 may include substrate 532. The first side 532a of substrate 532 may include conductive trace 534. A plurality of temperature sensors 538a/538b/538c may be coupled to conductive trace 534. The second side of substrate 532 may include a layer of conductive material 542. Layer 542 may be coupled to conductive trace 534 by via 536.

Figure 19:
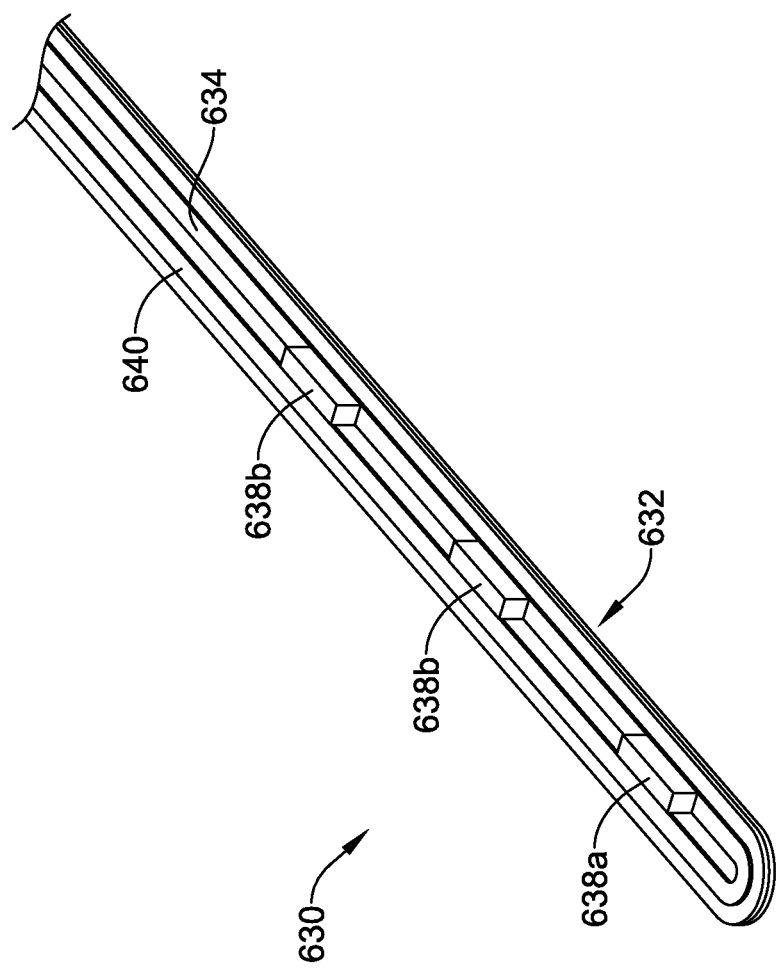
FIGS. 19-20 illustrate a portion of an example flexible circuit.
Figure 20:
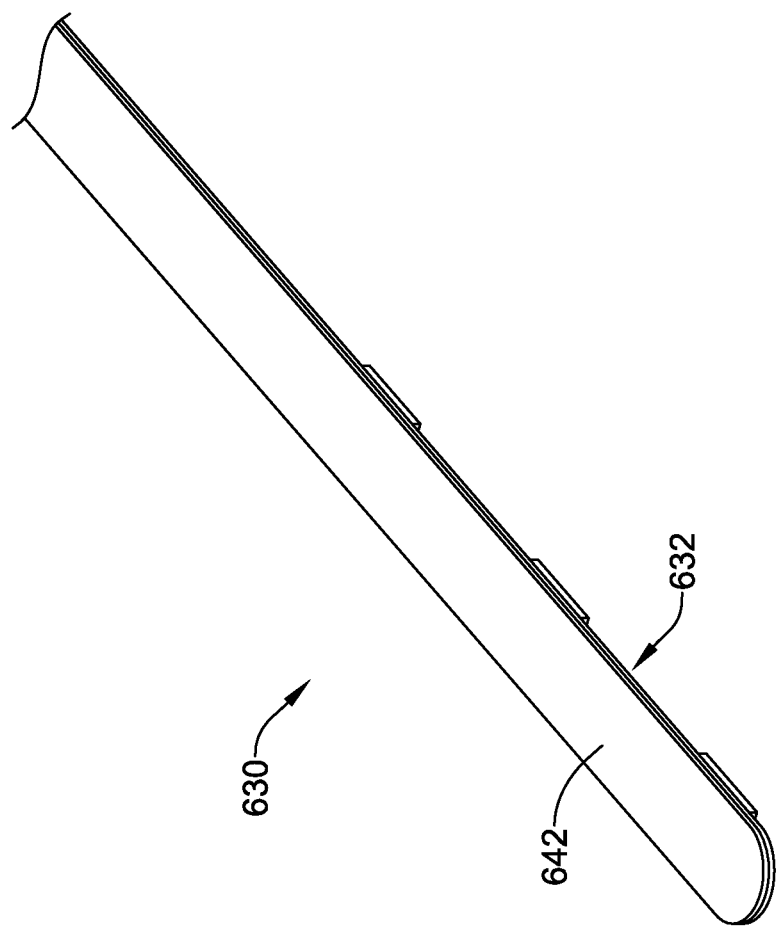

FIGS. 19-20 illustrate another example flexible circuit 630 that may be similar to other flexible circuits disclosed herein. Flexible circuit 630 may include substrate 332. Conductive trace 634 and return trace 640 may be disposed along first side 632a of substrate 632. A plurality of temperature sensor 638a/638b/638c may be coupled to traces 634/640. The second side of substrate 632 may include a layer of conductive material 642.

The materials that can be used for the various components of medical device 10 (and/or other medical devices disclosed herein) and the various tubular members disclosed herein may include those commonly associated with medical devices. For simplicity purposes, the following discussion makes reference to shaft 12 and other components of medical device 10. However, this is not intended to limit the devices and methods described herein, as the discussion may be applied to other tubular members and/or components of tubular members or devices disclosed herein.

Shaft 12 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of medical device 10 to achieve the same result.

In some embodiments, a degree of Magnetic Resonance Imaging (MRI) compatibility is imparted into medical device 10. For example, shaft 12 or portions thereof may be made of a material that does not substantially distort the image and create substantial artifacts (i.e., gaps in the image). Certain ferromagnetic materials, for example, may not be suitable because they may create artifacts in an MRI image. Shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of shaft 12 that may define a generally smooth outer surface for medical device 10. In other embodiments, however, such a sheath or covering may be absent from a portion of all of medical device 10, such that shaft 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the medical device 10 (including, for example, the exterior surface of shaft 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of shaft 12, or other portions of medical device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An ablation system, comprising:
   an elongate shaft having a distal region; and
   a plurality of electrically conductive ablation tines disposed at the distal region;
   wherein each of the plurality of ablation tines includes an electrically conductive tubular member having a flexible circuit disposed therein, wherein the tubular member has a length and is electrically conductive along an entirety of the length;
   wherein the flexible circuit of each ablation tine includes a substrate, one or more electrodes coupled to the substrate, and a temperature sensor coupled to the substrate and positioned adjacent to the one or more electrodes, the one or more electrodes of the flexible circuit being disposed within the tubular member and in electrical contact with the tubular member;
   wherein the plurality of ablation tines includes a first ablation tine and a second ablation tine; and
   wherein a pair of bipolar electrodes is defined by a first electrode disposed at the first ablation tine and a second electrode disposed at the second ablation tine.

2. The ablation system of claim 1, wherein the plurality of ablation tines includes a distal array of ablation tines and a proximal array of ablation tines.

3. The ablation system of claim 2, wherein the distal array of ablation tines is circumferentially offset from the proximal array of ablation tines.

4. The ablation system of claim 1, wherein the flexible circuit of each ablation tine includes a first trace disposed along a first side of the substrate, the first trace being coupled to the temperature sensor.

5. The ablation system of claim 4, wherein the flexible circuit of each ablation tine includes a second trace disposed along a second side of the substrate, the second trace being coupled to the first trace by a via.

6. The ablation system of claim 5, wherein the one or more electrodes coupled to the substrate are disposed along the second side of the substrate.

7. The ablation system of claim 1, wherein the flexible circuit includes an active trace disposed along a first side of the substrate, wherein the temperature sensor is coupled to the active trace, and wherein a return trace coupled to the active trace is disposed along the first side of the substrate.

8. The ablation system of claim 1, wherein the flexible circuit includes one or more additional temperature sensors.

9. The ablation system of claim 1, wherein the flexible circuit is folded within the tubular member.

10. The ablation system of claim 1, further comprising a processor coupled to the plurality of ablation tines.

11. The ablation system of claim 10, wherein the processor is capable of modulating power delivered to the pair of bipolar electrodes based on feedback from a temperature sensor.

12. An ablation system, comprising:
an elongate shaft having a distal region; and
a plurality of ablation tines disposed at the distal region;
wherein each of the plurality of ablation tines includes a conductive tubular member having a flexible circuit disposed therein, wherein the tubular member has a length and is electrically conductive along an entirety of the length;
wherein the flexible circuit of each ablation tine includes a substrate, a temperature sensor coupled to the substrate, and an electrode coupled to the substrate, the electrode being disposed within the tubular member and in electrical contact with the tubular member; and
wherein the plurality of ablation tines includes a first ablation tine and a second ablation tine that define a pair of bipolar electrodes.

13. A medical device for ablating tissue, the medical device comprising:
an elongate shaft having a distal region;
an array of distal ablation tines disposed along the distal region, each distal ablation tine including an electrically conductive tubular member, wherein the tubular member has a length and is electrically conductive along an entirety of the length;
an array of proximal ablation tines disposed adjacent to the distal ablation tines, each proximal ablation tine including a tubular member; and
a processor coupled to the array of distal ablation tines and to the array of proximal ablation tines;
wherein each tubular member has a flexible circuit disposed therein;
wherein the flexible circuit of each tubular member includes a substrate and a temperature sensor coupled to the substrate;
wherein the temperature sensor of each flexible circuit is positioned adjacent to an electrode disposed along the substrate, the electrode being electrically coupled to the tubular member and disposed within the tubular member, wherein the processor is capable of modulating power delivered to the electrode based on feedback from the temperature sensor;
wherein the array of distal ablation tines, the array of proximal ablation tines, or both are capable of shifting between a first configuration and an expanded configuration; and
wherein at least one pair of bipolar electrodes is defined within or across the arrays of distal and proximal ablation tines.

14. The medical device of claim 13, wherein the array of distal ablation tines is circumferentially offset from the array of proximal ablation tines.

15. The medical device of claim 13, wherein the flexible circuit of each tubular member further includes a first trace disposed along a first side of the substrate, the first trace being coupled to the temperature sensor.

16. The medical device of claim 15, wherein the flexible circuit of each tubular member further includes a second trace disposed along a second side of the substrate, the second trace being coupled to the first trace by a via.

17. The medical device of claim 16, wherein the electrode of each flexible circuit is disposed along the second side of the substrate.

18. The medical device of claim 13, wherein each flexible circuit is folded within the tubular member.

19. The medical device of claim 13, wherein the array of distal ablation tines and wherein the array of proximal ablation tines are composed of an electrically conductive material.

* * * * *